(12) United States Patent
Burgess et al.

(10) Patent No.: US 12,272,438 B2
(45) Date of Patent: Apr. 8, 2025

(54) MODULAR WITNESSING DEVICE

(71) Applicant: CareFusion 303, Inc., San Diego, CA (US)

(72) Inventors: Brendan John Burgess, Poway, CA (US); Magnus Roland Felke, San Diego, CA (US); Paul Anthony Preziotti, Coto de Caza, CA (US); Ramkumar Subramanian, San Diego, CA (US); Dugan Joyce, Chula Vista, CA (US); Mustafa Yusufi, Escondido, CA (US)

(73) Assignee: CareFusion 303, Inc., San Diego, CA (US)

( * ) Notice: Subject to any disclaimer, the term of this patent is extended or adjusted under 35 U.S.C. 154(b) by 307 days.

(21) Appl. No.: 17/183,128

(22) Filed: Feb. 23, 2021

(65) Prior Publication Data

US 2021/0265032 A1   Aug. 26, 2021

Related U.S. Application Data

(60) Provisional application No. 62/980,517, filed on Feb. 24, 2020.

(51) Int. Cl.
*G16H 20/13* (2018.01)
*A61J 1/14* (2023.01)
(Continued)

(52) U.S. Cl.
CPC ............ *G16H 20/13* (2018.01); *A61J 1/1437* (2013.01); *G16H 40/20* (2018.01); *G16H 40/40* (2018.01); *G16H 40/67* (2018.01)

(58) Field of Classification Search
CPC ........ G16H 20/13; G16H 40/20; G16H 40/40; G16H 40/67; A61J 1/1437; G06Q 10/06
See application file for complete search history.

(56) References Cited

U.S. PATENT DOCUMENTS 4,551,133 A   11/1985   Zegers de Beyl et al.
4,693,804 A   9/1987    Serwer
(Continued)

FOREIGN PATENT DOCUMENTS

AU   2017 279 693 A1   1/2018
AU   2018335288 B2    8/2023
(Continued)

OTHER PUBLICATIONS

CN110265108A—machine translation (Year: 2019).*
(Continued)

*Primary Examiner* — Jason S Tiedeman
(74) *Attorney, Agent, or Firm* — Mintz Levin Cohn Ferris Glovsky and Popeo, P.C.

(57) ABSTRACT

A method for remotely witnessing a medical workflow is provided. The method includes authenticating a clinician at a witnessing device. The method also includes receiving, at the witnessing device, a request to perform a medical workflow. The method further includes determining, at the witnessing device and based at least in part on the medical workflow, that a witness is required to observe the medical workflow. The method also includes initiating, at a witnessing client remotely coupled with the witnessing device, a witnessing session, wherein the witnessing client allows a witness to remotely observe the medical workflow. The method also includes enabling, in response to at least the initiation of the witnessing session, completion of the medical workflow. Related systems and articles of manufacture, including apparatuses and computer program products, are also disclosed.

17 Claims, 6 Drawing Sheets

(51) Int. Cl.
  *G16H 40/20* (2018.01)
  *G16H 40/40* (2018.01)
  *G16H 40/67* (2018.01)

(56) References Cited

U.S. PATENT DOCUMENTS

| | | |
|---|---|---|
| 5,945,651 A | 8/1999 | Chorosinski et al. |
| 5,961,036 A | 10/1999 | Michael et al. |
| 5,991,731 A | 11/1999 | Colon et al. |
| 6,113,578 A | 9/2000 | Brown |
| 6,650,964 B2 | 11/2003 | Spano, Jr. et al. |
| 6,671,579 B2 | 12/2003 | Spano, Jr. et al. |
| 6,842,736 B1 | 1/2005 | Brzozowski |
| 6,868,344 B1 | 3/2005 | Nelson |
| 7,119,689 B2 | 10/2006 | Mallett et al. |
| 7,184,897 B2 | 2/2007 | Nelson |
| 7,275,645 B2 | 10/2007 | Mallett et al. |
| 7,303,081 B2 | 12/2007 | Mallett et al. |
| 7,311,207 B2 | 12/2007 | Mallett et al. |
| 7,318,529 B2 | 1/2008 | Mallett et al. |
| 7,562,025 B2 | 7/2009 | Mallett et al. |
| 7,693,603 B2 | 4/2010 | Higham |
| 8,147,479 B1 | 4/2012 | Wach et al. |
| 8,195,328 B2 | 6/2012 | Mallett et al. |
| 8,280,550 B2 | 10/2012 | Levy et al. |
| 8,319,669 B2 | 11/2012 | Weller |
| 8,357,114 B2 | 1/2013 | Poutiatine et al. |
| 8,595,021 B2 | 11/2013 | Mallett et al. |
| 8,606,596 B1 | 12/2013 | Bochenko et al. |
| 8,725,532 B1 | 5/2014 | Ringold |
| 8,738,177 B2 | 5/2014 | van Ooyen et al. |
| 8,768,724 B2 | 7/2014 | Whiddon et al. |
| 8,905,964 B2 | 12/2014 | Poutiatine et al. |
| 9,158,892 B2 | 10/2015 | Levy et al. |
| 9,202,052 B1 | 12/2015 | Fang et al. |
| 9,227,025 B2 | 1/2016 | Butterfield et al. |
| 9,354,178 B2 | 5/2016 | Lee |
| 9,427,520 B2 | 8/2016 | Batch et al. |
| 9,456,958 B2 | 10/2016 | Reddy et al. |
| 9,523,635 B2 | 12/2016 | Tilden |
| 9,636,273 B1 | 5/2017 | Harris |
| 9,752,935 B2 | 9/2017 | Marquardt et al. |
| 9,796,526 B2 | 10/2017 | Smith et al. |
| 9,817,850 B2 | 11/2017 | Dubbels et al. |
| 9,836,485 B2 | 12/2017 | Dubbels et al. |
| 9,842,196 B2 | 12/2017 | Utech et al. |
| 9,881,129 B1 | 1/2018 | Cave |
| 9,958,324 B1 | 5/2018 | Marquardt et al. |
| 10,032,344 B2 | 7/2018 | Nelson et al. |
| 10,101,269 B2 | 10/2018 | Judge et al. |
| 10,187,288 B2 | 1/2019 | Parker et al. |
| 10,209,176 B2 | 2/2019 | Proskurowski et al. |
| 10,241,038 B2 | 3/2019 | Nishimura et al. |
| 10,249,153 B2 | 4/2019 | Nelson et al. |
| 10,309,832 B2 | 6/2019 | Marquardt et al. |
| 10,345,242 B2 | 7/2019 | Zhao et al. |
| 10,580,525 B2 | 3/2020 | Adams et al. |
| 10,832,207 B2 | 11/2020 | Vahlberg et al. |
| 11,037,666 B1 | 6/2021 | Benoit et al. |
| 11,116,892 B2 | 9/2021 | Brady et al. |
| 11,147,914 B2 | 10/2021 | Estes |
| 11,481,739 B1 | 10/2022 | McKinzie |
| 2003/0158751 A1 | 8/2003 | Suresh et al. |
| 2003/0167190 A1 | 9/2003 | Rincavage et al. |
| 2005/0277873 A1 | 12/2005 | Stewart et al. |
| 2006/0064053 A1 | 3/2006 | Bollish et al. |
| 2007/0260487 A1 | 11/2007 | Bartfeld et al. |
| 2008/0059226 A1 | 3/2008 | Melker et al. |
| 2008/0082360 A1 | 4/2008 | Bailey et al. |
| 2008/0140715 A1 | 6/2008 | Hakos |
| 2008/0243055 A1 | 10/2008 | Fathallah et al. |
| 2008/0288430 A1 | 11/2008 | Friedlander et al. |
| 2008/0306796 A1 | 12/2008 | Zimmerman et al. |
| 2008/0319795 A1 | 12/2008 | Poteet et al. |
| 2009/0083231 A1 | 3/2009 | Eberholst et al. |
| 2009/0160646 A1 | 6/2009 | Mackenzie et al. |
| 2010/0042437 A1* | 2/2010 | Levy ............... G16H 40/67 700/242 |
| 2010/0169063 A1 | 7/2010 | Yudkovitch et al. |
| 2010/0213250 A1 | 8/2010 | Mallett et al. |
| 2010/0271218 A1 | 10/2010 | Hoag et al. |
| 2011/0016110 A1 | 1/2011 | Egi et al. |
| 2011/0082440 A1 | 4/2011 | Kimmo et al. |
| 2011/0161108 A1 | 6/2011 | Miller et al. |
| 2012/0173440 A1 | 7/2012 | Dehlinger et al. |
| 2012/0226447 A1 | 9/2012 | Nelson et al. |
| 2012/0265336 A1 | 10/2012 | Mallett et al. |
| 2012/0305132 A1 | 12/2012 | Maness |
| 2012/0325330 A1 | 12/2012 | Prince et al. |
| 2013/0002429 A1 | 1/2013 | Johnson |
| 2013/0018356 A1 | 1/2013 | Prince et al. |
| 2013/0070090 A1* | 3/2013 | Bufalini ............ G16H 20/13 348/143 |
| 2013/0144254 A1 | 6/2013 | Amirouche et al. |
| 2013/0158705 A1 | 6/2013 | Levy et al. |
| 2013/0253291 A1* | 9/2013 | Dixon ............... A61B 90/98 600/323 |
| 2013/0253700 A1 | 9/2013 | Carson et al. |
| 2013/0262138 A1 | 10/2013 | Jaskela et al. |
| 2013/0282392 A1 | 10/2013 | Wurm |
| 2013/0325721 A1 | 12/2013 | MacDonell et al. |
| 2014/0074284 A1 | 3/2014 | Czaplewski et al. |
| 2014/0081652 A1 | 3/2014 | Klindworth |
| 2014/0149131 A1 | 5/2014 | Bear et al. |
| 2014/0249776 A1 | 9/2014 | King et al. |
| 2014/0277707 A1 | 9/2014 | Akdogan et al. |
| 2014/0375324 A1 | 12/2014 | Matsiev et al. |
| 2015/0038898 A1 | 2/2015 | Palmer et al. |
| 2015/0061832 A1* | 3/2015 | Pavlovic ............ G07C 9/00896 340/5.83 |
| 2015/0081324 A1 | 3/2015 | Adjaoute |
| 2015/0109437 A1 | 4/2015 | Yang et al. |
| 2015/0161558 A1* | 6/2015 | Gitchell ............ G06Q 50/22 235/375 |
| 2015/0221086 A1* | 8/2015 | Bertram ............ G16H 20/13 382/128 |
| 2015/0272825 A1 | 10/2015 | Lim et al. |
| 2015/0286783 A1 | 10/2015 | Kumar et al. |
| 2015/0294079 A1* | 10/2015 | Bergougnan ........ G16H 20/10 705/2 |
| 2015/0323369 A1 | 11/2015 | Marquardt |
| 2015/0339456 A1 | 11/2015 | Sprintz |
| 2015/0362350 A1 | 12/2015 | Miller et al. |
| 2016/0034274 A1 | 2/2016 | Diao et al. |
| 2016/0062371 A1 | 3/2016 | Davidian et al. |
| 2016/0117478 A1* | 4/2016 | Hanina ............... G16H 10/60 705/3 |
| 2016/0161705 A1 | 6/2016 | Marquardt et al. |
| 2016/0166766 A1 | 6/2016 | Schuster et al. |
| 2016/0259904 A1 | 9/2016 | Wilson |
| 2016/0259911 A1* | 9/2016 | Koester ............. G16Z 99/00 |
| 2016/0283691 A1 | 9/2016 | Ali |
| 2016/0346469 A1 | 12/2016 | Shubinsky et al. |
| 2017/0017760 A1 | 1/2017 | Freese et al. |
| 2017/0032102 A1 | 2/2017 | Skoda |
| 2017/0076065 A1 | 3/2017 | Darr et al. |
| 2017/0083681 A1* | 3/2017 | Sprintz ............. G16H 20/10 |
| 2017/0103203 A1 | 4/2017 | Sharma et al. |
| 2017/0108480 A1 | 4/2017 | Clark et al. |
| 2017/0109673 A1* | 4/2017 | Vahlberg ........... G07F 9/002 |
| 2017/0109497 A1 | 4/2017 | Tribble et al. |
| 2017/0120035 A1 | 5/2017 | Butterfield et al. |
| 2017/0199983 A1 | 7/2017 | Cano et al. |
| 2018/0028408 A1 | 2/2018 | Li et al. |
| 2018/0039736 A1* | 2/2018 | Williams ........... G16H 10/60 |
| 2018/0046651 A1 | 2/2018 | Dubbels et al. |
| 2018/0157803 A1 | 6/2018 | Mirov |
| 2018/0165417 A1* | 6/2018 | Hall ................. A61B 5/6891 |
| 2018/0192942 A1 | 7/2018 | Clark et al. |
| 2018/0203978 A1 | 7/2018 | Basu et al. |
| 2018/0231415 A1 | 8/2018 | Marquardt et al. |
| 2018/0247703 A1 | 8/2018 | D'Amato |
| 2018/0259446 A1 | 9/2018 | Coffey et al. |

(56) References Cited

U.S. PATENT DOCUMENTS

| | | |
|---|---|---|
| 2018/0299375 A1 | 10/2018 | Young et al. |
| 2018/0330824 A1 | 11/2018 | Athey et al. |
| 2018/0365385 A1 | 12/2018 | Cooney et al. |
| 2018/0365386 A1 | 12/2018 | Vanderveen |
| 2019/0088354 A1 | 3/2019 | Yanowitz et al. |
| 2019/0117883 A1 | 4/2019 | Abrams et al. |
| 2019/0124118 A1 | 4/2019 | Swafford |
| 2019/0139638 A1* | 5/2019 | Keefe .................... G16H 20/13 |
| 2019/0180862 A1 | 6/2019 | Wisser et al. |
| 2019/0244699 A1 | 8/2019 | Loebig et al. |
| 2019/0247703 A1 | 8/2019 | Welde et al. |
| 2019/0341142 A1 | 11/2019 | Nag et al. |
| 2019/0355461 A1* | 11/2019 | Kumar .................... G16H 10/60 |
| 2020/0085686 A1 | 3/2020 | Aliakbarian et al. |
| 2020/0098474 A1 | 3/2020 | Vanderveen |
| 2020/0219611 A1 | 7/2020 | Nag et al. |
| 2020/0222627 A1 | 7/2020 | Guerra et al. |
| 2020/0230316 A1 | 7/2020 | Guerra et al. |
| 2020/0312442 A1 | 10/2020 | Hairr et al. |
| 2020/0402632 A1 | 12/2020 | van Schelven et al. |
| 2021/0005324 A1 | 1/2021 | Bostic et al. |
| 2021/0027259 A1 | 1/2021 | Burgess et al. |
| 2021/0133201 A1 | 5/2021 | Tribble et al. |
| 2021/0249121 A1 | 8/2021 | Burgess et al. |
| 2021/0308385 A1 | 10/2021 | Nisha et al. |
| 2022/0005574 A1 | 1/2022 | Kühn |
| 2022/0062964 A1 | 3/2022 | VanDerWoude et al. |
| 2022/0093239 A1 | 3/2022 | Nag et al. |
| 2022/0254470 A1 | 8/2022 | LaFauci et al. |

FOREIGN PATENT DOCUMENTS

| | | | |
|---|---|---|---|
| CA | 2561239 C * | 2/2010 | ......... G07F 17/0092 |
| CA | 2 636 115 C | 6/2014 | |
| CA | 2 848 274 C | 9/2016 | |
| CN | 106687960 A | 5/2017 | |
| CN | 110265108 A * | 9/2019 | |
| EP | 1 973 593 B1 | 4/2013 | |
| EP | 1 593 076 B1 | 10/2019 | |
| JP | 2007-304654 A | 11/2007 | |
| JP | 2016-517077 A | 6/2016 | |
| JP | 2018-181340 A | 11/2018 | |
| KR | 10-2014-0129141 A | 11/2014 | |
| WO | WO-2006/034367 A2 | 3/2006 | |
| WO | WO-2010/058796 A1 | 5/2010 | |
| WO | WO-2011/014517 A1 | 2/2011 | |
| WO | WO-2011/035277 A1 | 3/2011 | |
| WO | WO-2011039676 A2 * | 4/2011 | ........... A61B 5/0002 |
| WO | WO-2014/055925 A1 | 4/2014 | |
| WO | WO-2015/187682 A1 | 12/2015 | |
| WO | WO-2019/028004 A1 | 2/2019 | |
| WO | WO-2019/031331 A1 | 2/2019 | |
| WO | WO-2020206154 A1 * | 10/2020 | ......... G06Q 10/0631 |
| WO | WO-2020/251962 A1 | 12/2020 | |

OTHER PUBLICATIONS

Benjamin, X.C. et al. (2012). "Visual identification of medicine boxes using features matching." *IEEE International Conference on Virtual Environments Human-Computer Interfaces and Measurement Systems (VECIMS) Proceedings*, 43-47. Doi: 10.1109/VECIMS.2012.6273190.

Cakaloglu, T. (Nov. 1, 2017). "Medi-Deep: Deep control in a medication usage." *2017 IEEE International Conference of Bioinfomratice and Biomedicine (BIBM)*, 899-904. Doi: 10.1109/BIBM.2017.8217776.

Neuman, M.R. et al. (May 13, 2012), "Advances in Medical Devices and Medical Electronics," in Proceedings of the IEEE, vol. 100, No. Special Centennial Issue, pp. 1537-1550,doi: 10.1109/JPROC.2012.2190684.

Qui et al. (2016) "A survey of machine learning for big data processing." *EURASIP Journal on Advances in Signal Processing*, Article No. 67, 16 pages.

Shishvan, O. Rajabi et al. (2018). "Machine Intelligence in Healthcare and Medical Cyber Physical Systems: A Survey." *IEEE Access*. vol. 6, 46419-46494. doi: 10.1109/ACCESS.2018.2866049.

Uniyal, D. et al. (Nov. 7, 2014), "Pervasive Healthcare—A Comprehensive Survey of Tools and Techniques," arXiv: 1411.1821v1, 48 pages.

Yang, J., McAuley, J.J., & Leskovec, J. (2013). "Community Detection in Networks with Node Attributes." 2013 IEEE 13th International Conference on Data Mining, 1151-1156.

Yaniv, Z. et al. (Oct. 1, 2016). "The National Library of Medicine Pill Image Recognition Challenge: An Initial Report." *Oct. 2016 IEEE Applied Imagery Pattern Recognition Workshop, (AIPR)*, 1-9. Doi: 10.1109/AIPR.2016.8010584.

Zhan, A. et al. (Jan. 5, 2016) "High Frequency Remote Monitoring of Parkinson's Disease via Smartphone: Platform Overview and Medication Response Detection," Retrieved Apr. 29, 2021. 12 pages.

* cited by examiner

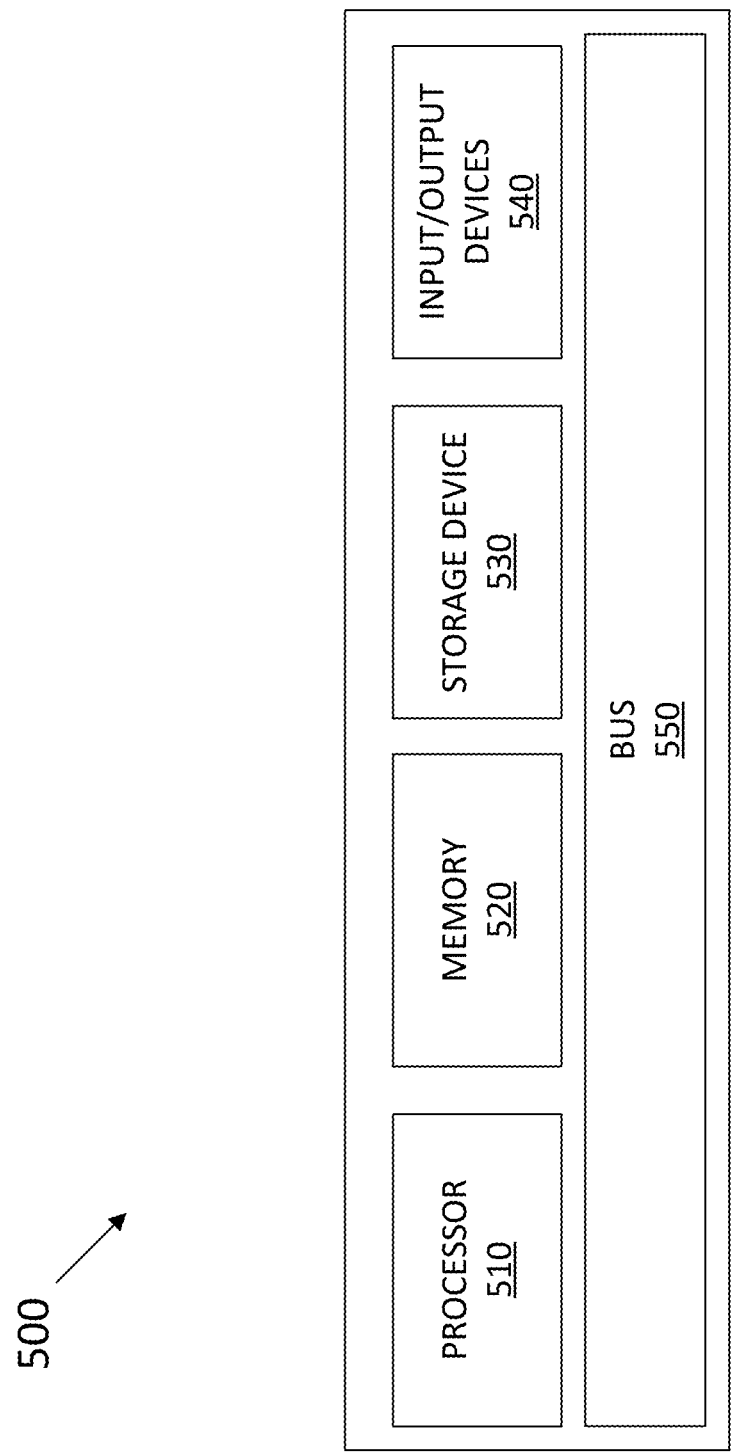

MODULAR WITNESSING DEVICE

CROSS-REFERENCE TO RELATED APPLICATIONS

The present application claims priority to U.S. Provisional Application No. 62/980,517, filed on Feb. 24, 2020, and entitled "Modular Witnessing Device," the entirety of which is incorporated by reference herein.

TECHNICAL FIELD

The subject matter described herein relates generally to a modular witnessing system for remotely witnessing one or more medical workflows.

BACKGROUND

Diversion may refer to the transfer of a controlled substance to a third party who is not legally authorized to receive, possess, and/or consume the controlled substance. High-value and/or controlled prescription medications, notably opioids, may be especially prone to diversion. For instance, prescription medications may be diverted while being loaded into and/or retrieved from a dispensing cabinet. Some prescription medications, such as morphine, hydromorphone, fentanyl, and/or the like, may be administered to a patient via a pump, for example, a patient-controlled analgesic (PCA) pump, that is capable of holding more doses of the prescription medication than is needed by the patient or administering partial doses for a patient. The extra or residual doses of prescription medication may be susceptible to being diverted by the clinicians. For example, some of the prescription medication may be removed before being loaded into the pump. Alternatively and/or additionally, prescription medication that remains in the pump may be held back instead of properly disposed of at a wasting site and/or may be improperly disposed at the wasting site. Additionally and/or alternatively, witnessed patient consent may be required before administration of certain types of medications and/or before certain medical procedures. Accordingly, a witness may be required to observe certain medical workflows.

SUMMARY

Systems, methods, and articles of manufacture, including computer program products, are provided for remotely witnessing, via a witnessing device, at least one medical workflow, such as the wasting of medications, dispensation of medications, administration of medications, and/or obtaining of consent from a patient. The at least one medical workflow may include use of at least one companion device communicatively coupled with the witnessing device.

According to some aspects, a method may be provided. The method may include authenticating, at a witnessing device, a clinician. The method may also include receiving, at the witnessing device, a request to perform a medical workflow. The method may further include determining, at the witnessing device and based at least in part on the medical workflow, a witness is required to observe the medical workflow. The method may also include initiating, at a witnessing client coupled with the witnessing device, a witnessing session. The witnessing client may allow the witness to remotely observe the medical workflow. The method may also include enabling, in response to at least the initiation of the witnessing session, completion of the medical workflow.

In some aspects, enabling completion of the medical workflow includes communicating with at least one companion device associated with the medical workflow to trigger a completion event at the at least one companion device.

In some aspects, the completion event includes unlocking the at least one companion device to allow access to the at least one companion device.

In some aspects, the at least one companion device includes one or more of a smart lock, a waste container, a dispensing cabinet, and a camera.

In some aspects, enabling completion of the medical workflow includes displaying, via a user interface coupled with the witnessing device, a prompt to the clinician. The prompt may include instructions for completing the medical workflow.

In some aspects, the medical workflow includes one or more of: wasting a medication, dispensing a medication, administering a medication, and obtaining consent from a patient.

In some aspects, authenticating the clinician includes verifying an identity of the clinician as an authorized user.

In some aspects, the determination that the witness is required to observe the medical workflow is based at least on a type of medication involved in the medical workflow.

In some aspects, the determination that the witness is required to observe the medical workflow is based at least on the clinician performing the medical workflow.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 5 depicts a block diagram illustrating a computing system consistent with implementations of the current subject matter.

When practical, similar reference numbers denote similar structures, features, or elements.

DETAILED DESCRIPTION

Figure 1A:
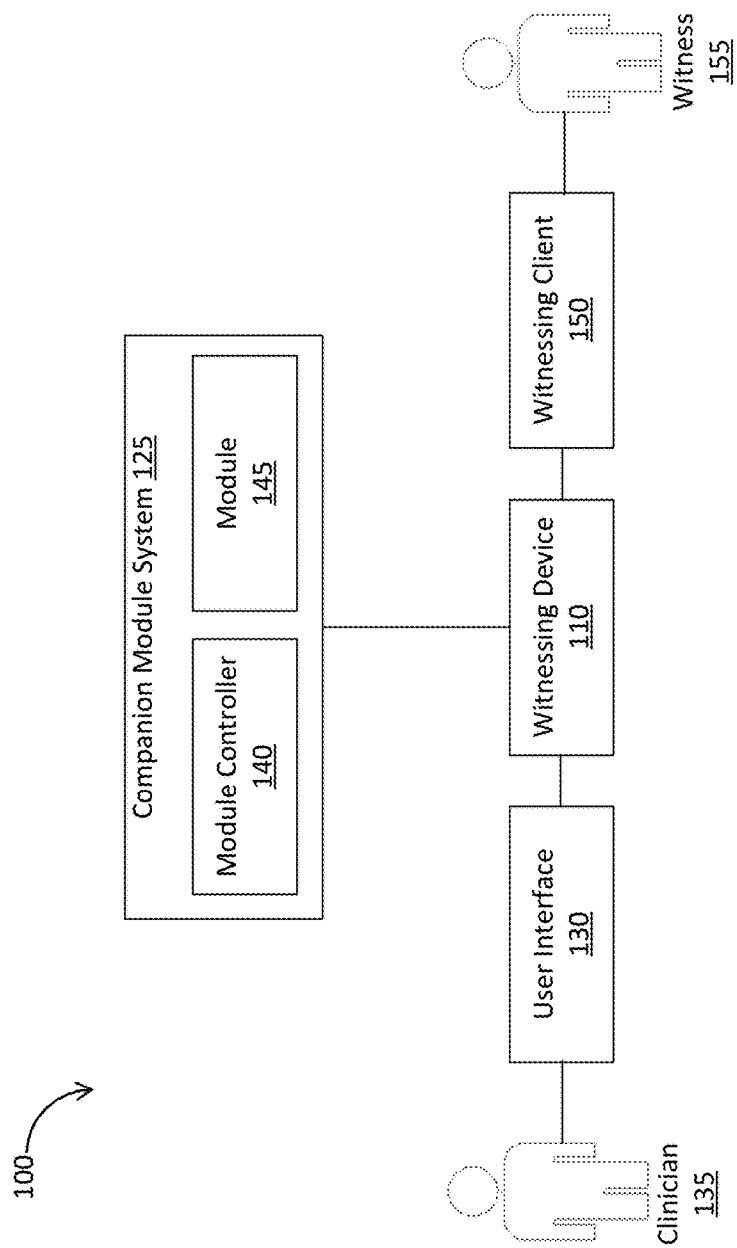
FIG. 1A and FIG. 1B are system diagrams depicting aspects of a witnessing system consistent with implementations of the current subject matter.

Diversion of a medication may occur at any point in time including, for example, during the shipping, receiving, stocking, dispensing, administering, or wasting of the medication. Prescription pain medication may be especially prone to diversion due to a lack of sufficient custodial oversight, for example, during the shipping, receiving, stocking, dispensing, administering, or wasting of the prescription pain medication. For example, dispensing cabinets and/or wasting stations at medical facilities may be accessible to multiple clinicians or other personnel or users. Moreover, different users may be responsible for different aspects of dispensing, administering, and/or wasting of the medication. Thus, even when diversion is detected, it may be difficult to determine when the diversion actually occurred and to further identify the person or persons responsible for the diversion.

A witness (in addition to the clinician) may be required to view certain medical workflows, such as wasting medications, dispensing medications, administering medications, and/or obtaining consent from a patient. Additionally and/or alternatively, a witness may be required to observe medical workflows involving a certain type of medication (e.g., a controlled and/or hazardous medication), a particular clinician (e.g., a clinician with particular credentials, training, history, and/or the like), and/or a particular patient (e.g., a patient under or over a certain age, with a particular medical history and/or the like). However, medical facilities may be under-staffed, may be busy, and/or may have limited space available. Thus, obtaining a live witness to view the medical workflow at the location of the medical workflow may be difficult and live witnesses may be unavailable at the medical facility. Even in situations when a live witness may be obtained, it may be difficult to track various aspects of the witnessed medical workflow, such as the time of the medical workflow, what medication was involved, where the medication was placed, who was involved in the medical workflow, and/or the like. Additionally, in some circumstances, clinicians and/or witnesses may engage in so-called "predatory" procedures (e.g., when wasting medications), in which a clinician routinely selects the same clinician to witness the medical workflow and/or in which a group of clinicians routinely serve as each other's witness during the medical workflow. As described herein, a medical workflow may refer to a series of one or more steps to complete a medical-related task, such as wasting medications, dispensing medications, administering medications, obtaining consent from a patient, and/or the like.

To provide incentives to not engage in predatory or improper practices, such as the diversion of medication and/or improper wasting of medication, and to identify clinicians or other users who may be engaged in the predatory practices, a witnessing system consistent with implementations of the current subject matter includes a witnessing device and a modular companion system including at least one modular companion device. The witnessing device includes features for securely witnessing the medical workflow including the receipt and storage of wasted medication. The witnessing device may communicate with the at least one modular companion device, including smart locks, waste containers, dispensing cabinets, cameras, and/or the like, during a witnessing session at the witnessing device. Accordingly, the witnessing system described herein may help to reduce or eliminate the possibility that a witness will be unavailable during a medical workflow, reduce or eliminate predatory medical practices, and/or reduce or eliminate diversion of medication. The witnessing system described herein may also produce verifiable records of various aspects of the witnessed medical workflow, which provides an audit trail of the witnessing, including, for example, recorded video, images, audio, and/or other data associated with the medical workflow. The witnessing device described herein may also communicate with at least one modular companion device or module within the patient care area, which may help clinicians properly dispose of medication, capture various views of the medical workflow, and/or the like. The witnessing device described herein may also provide instructions to the clinician and/or witness to help ensure that the medical workflow is performed properly.

FIG. 1A depicts a system diagram illustrating a witnessing system 100 consistent with implementations of the current subject matter. Referring to FIG. 1A, the witnessing system 100 includes a witnessing device 110, a user interface 130 accessible to a clinician 135, and a witnessing client 150 accessible to a witness 155. The user interface 130 and the witnessing client 150 may be communicatively coupled to the witnessing device 110, for example, via a network. In some implementations, the user interface 130 may be part of and/or integrated with the witnessing device 110. The witnessing device 110, the user interface 130, and the witnessing client 150 may be implemented as or include processor-based devices, for example, a smartphone, a tablet computer, a wearable apparatus, a desktop computer, a laptop computer, a workstation, or the like. The network may be a wired and/or wireless network including, for example, a public land mobile network (PLMN), a local area network (LAN), a virtual local area network (VLAN), a wide area network (WAN), the Internet, a short range radio connection, for example a BLUETOOTH® compatible connection, a peer-to-peer mesh network, or the like.

In some implementations, the witnessing system 100 also includes a companion module system 125, which includes at least one companion module 145 and a module controller 140, which controls one or more operations of the at least one companion module 145 and communicates with the witnessing device 110. The at least one companion module 145 may include a smart lock, various waste collection bins and/or stations (e.g., a modular individual liquid collector, a modular bulk liquid collector, a modular individual solid collector, a modular bulk solid collector, and/or the like), and one or more recording devices (e.g., video cameras, image cameras, and/or the like). The witnessing device 110 may communicate with the companion module system 125 to cause the at least one companion module 145 to perform certain operations, such as opening, closing, locking, unlocking, recording, and the like, during the medical workflow and/or witnessing session.

Consistent with implementations of the current subject matter, the witnessing client 150 allows for the witness 155 to remotely observe, via the witnessing device 110, one or more medical workflows, including wasting medications, dispensing medications, administering medications, obtaining consent from a patient, and/or the like. As used herein, the "wasting" of a medication may refer to the disposal of a substance in accordance with institutional guidelines and/or government regulations. For example, the proper wasting of a prescription pain medication may require the controlled substance to be collected in a designated receptacle (e.g., wasting stations) while in the presence of one or more witnesses, such as the witness 155.

The witnessing client 150 may be in communication with the witnessing device 110 over one or more of: a local area network, a wireless connection, or a direct connection. The witnessing client 150 may include, for example, a laptop computer or a dedicated computer that allows the witness 155 to observe at least one medical workflow taking place at or near the witnessing device 110. In some implementations, the witnessing client 150 is cloud-based. In some implementations, the witnessing client 150 may be located at a physical location (e.g., a remote pharmacy, medical facility, room, building, or other facility) that is separate from the witnessing device 110, allowing the witness 155 to observe the wasting process remotely, for example, using a camera on or in communication with the witnessing device 110. As such, the witnessing client 150 may reduce or eliminate the need to seek an authorized witness 155 to observe the medical workflow in real-time at the witnessing device 110. This may allow the witness to remotely observe the medical workflow while the remote witness is located at a different physical location, such as at a pharmacy, medical facility, room, same building, different building, and/or other facility, than the location where the medical workflow is being performed.

The witnessing client 150 may request credentials from the witness 155 or otherwise authenticate the witness 155. For example, the witnessing client 150 may prompt, via a user interface of the witnessing client 150, the witness 155 enter a user name and password, scan a badge using a card reader, perform a fingerprint scan or a retina scan, and/or use facial recognition to identify the witness 155. The witnessing client 150 may transmit a control message to the witnessing device 110 to collect the credential information. For example, the control message may activate a scanning device (e.g., camera, badge reader, optical scanner, etc.) associated with the witnessing device 110 or cause display of a user interface to collect the credential information. The witnessing client 150 may include a display that is updated with actions performed by the clinician 135 during the wasting process. The witnessing client 150 may include the ability to communicate, view, and/or record the medical workflow. Records captured at the witnessing client 150 and/or the witnessing device 110 may be stored and used during an audit of the medical workflow.

Consistent with implementations of the current subject matter, the user interface 130 may be in communication with and/or form a part of the witnessing device 110, such as via a local area network, a wireless connection, and/or a direct connection. The user interface 130 may include, for example, a display, a touch display, a keyboard, a mouse, one or more cameras, a card reader, a barcode scanner, a retina scanner, and/or a fingerprint scanner.

The witnessing system 100 may include features to ensure coordination between the witnessing client 150 and the witnessing device 110. For example, when remotely witnessing an event, the witness may require certain verifications that what is being witnessed and attested to is actually what is happening. Further, the witnessing system 100 may coordinate the collection of event information (e.g., scans, credential presentation, authentication, authorization, waste container location, wasting station operational state, connectivity status (e.g., connection, disconnection, retry attempt), etc.). Accordingly, the witnessing system 100 may include features to provide assurance to the users that the remote witnessing is secured and authentic along with features to capture and correlate the information collected by the separate devices (e.g., the witnessing client 150, the witnessing device 110, and the at least one companion module 145).

The witnessing system 100 may establish a secure communication channel between the witnessing client 150 and the witnessing device 110. The secure communication channel may include applying a digital signature or other authentication key that verifies the integrity of the information exchanged via the session. The witnessing client 150 may detect that the secure channel is established with the witnessing device 110 and provide a perceivable indication of the secure session on a display for the witnessing client 150. Similarly, the witnessing device 110 may determine that a secure channel is established with the witnessing client 150 and provide a perceivable indication of the secure session on a display for the witnessing client 150. The perceivable indication may include displaying an icon, changing a color on the user interface (e.g., the frame), activating a light on the device, emitting an audible tone, or some combination of these or similar indicators. The detection of a secure session may be based on protocol messaging or information included in a message received from another device participating in the session.

The witnessing client 150 and the witnessing device 110 may each present time information on respective displays. In this fashion, the users can confirm temporal synchronization of the two systems. The time information may be used to audit events during the witnessing session such as audio, video, or image data capture during the witnessing session. The time information may be encoded into the data captured during the witnessing session. For example, video data of the clinician and the witness may include a time stamp in the images and/or videos captured. The time stamps can further enhance the security of the witnessing session.

The event information for the witnessing session may be submitted by the witnessing client 150 and the witnessing device 110 using a distributed ledger or other secure logging technology such as a blockchain ledger. Once the witnessing session is established, a unique identifier may be generated by the system. The unique identifier may be used as part of records submitted to the distributed ledger along with the time information. The distributed ledger may then serve as an authoritative record of the events for the witnessing session.

A clinician 135, for example, a doctor, nurse, or other staff member or personnel (also referred herein as a user), may interact with the user interface 130 to access the functions of the witnessing device 110 and/or the at least one companion module 145 of the companion module system 125. The user interface 130 may display prompts on the display and/or accept inputs from the clinician 135 to guide the clinician 135 through the medical workflow, thereby confirming each step is complete, secure, and auditable.

The user interface 130 may authenticate the clinician 135 prior to allowing the clinician 135 to use the witnessing device 110. For example, the user interface 130 may prompt the clinician 135 for a username and password or other identifying information. Alternatively or additionally, the user interface 130 may read the clinician's badge using a card reader. Alternatively or additionally, the user interface 130 may obtain biometric information from the clinician 135 including, for example, a retina scan, fingerprint scan, and/or facial recognition features.

Referring to FIG. 1A, the at least one companion module 145 may be used to securely collect and store waste and/or one or more waste containers as part of a medical work flow. The at least one companion module 145 may be configured to receive and handle the waste, which may be medication in the form of solids or liquids or medication dispensers or applicators, for example, syringes or patches. Alternatively and/or additionally, the at least one companion module 145 may be configured to receive and handle one or more waste containers, in which medication in the form of solids or liquids or medication dispensers or applicators is contained.

In some implementations, the at least one companion module 145 may have multiple access points for the clinician to access during the medical workflow. An access point may be formed in the housing of one or more of the companion modules 145. The access point may be mechanically secured to prevent insertion of unauthorized items through the access point. For example, at the appropriate time during an authorized witnessing session, the witnessing device 110 may transmit a control message to (e.g., directly or via the module controller 140) a motor or other access control element to allow submission of waste via the access point. The access point may include a scanner or other sensor (e.g., light sensor) to determine when a container has passed into the module 145. The scanner or sensor may, in some implementations, be located separate from but proximate to the access point to achieve a similar detection. Once a submission is detected, the access control element may be activated to secure the access point from further submissions. Information from the sensor may be logged as an additional event during the witnessing session. The information may include duration of submission (e.g., as a proxy for length of the item submitted), duration the access point was unsecured, color or other optical property of the item submitted (e.g., was the wasting container of the expected color, reflectiveness, etc.), or information determined therefrom.

Consistent with implementations of the current subject matter, the witnessing device 110 may cause the companion module system 125 to dispense a waste container to be used during the medical workflow and/or indicate which module of the at least one companion module 145 should be used during the medical workflow. For example, the user interface 130 may prompt the clinician 135 to place and/or pour waste into one or more of the companion modules 145, for example, based on a number of factors including contents of the waste, testing that will be performed on the waste, temperature or light sensitivity of the waste, physical dimensions of the waste, volume of the waste, and/or other detectable or known properties and/or characteristics of the waste. The at least one companion module 145 for solids may include, for example, a plastic pouch, a bag, or other container. The at least one companion module 145 for liquids may include, for example, a vial, a syringe, or other container.

The at least one companion module 145 may include a sensing device. The sensing device may detect or otherwise provide a perceivable indication of when one or more of the companion modules 145 is opened and/or closed. The sensing device may maintain an event log that may be used to determine when the one or more of the companion modules 145 was opened and/or closed. For example, the sensing device may include a light activated pigment that will change color to indicate exposure to light and thereby indicate opening. The sensing device may include a physical tab or flange disposed on a surface of the one or more of the companion modules 145. Closing the one or more of the companion modules 145 may cause the tab or flange to move from a first position to a second position. In the second position, the substance within the one or more of the companion modules 145 may only be accessed by either destructive force to the entire companion module 145 or by breaking the tab or flange. The state of container and the tab or flange may be inspected to determine whether the one or more of the companion modules 145 were tampered with after depositing the substance. In some implementations, the sensing device may include an electrical element such as a programmable RFID tag to record information about the container. In some implementations, the one or more of the companion modules 145 may include a microprocessor or other programmable logic. For certain high value medications, such waste containers may be desirable to ensure tracking of the substance. The witnessing device 110 may selectively identify a type of module 145 to be used based on the medication included in the medical workflow, such as the substance identified for wasting. The one or more of the companion modules 145 may be dynamically programmed for tracking and tamper detection specific to one or more of: the wasting user, witnessing user, wasting location, substance being wasted, or other property detectable or accessible by the witnessing device 110. For example, some substances may not degrade with temperature variation. When wasting such substances, the witnessing device 110 may select a particular module 145 that does not include temperature sensor or program the waste container to disable temperature sensing features.

Figure 1B:
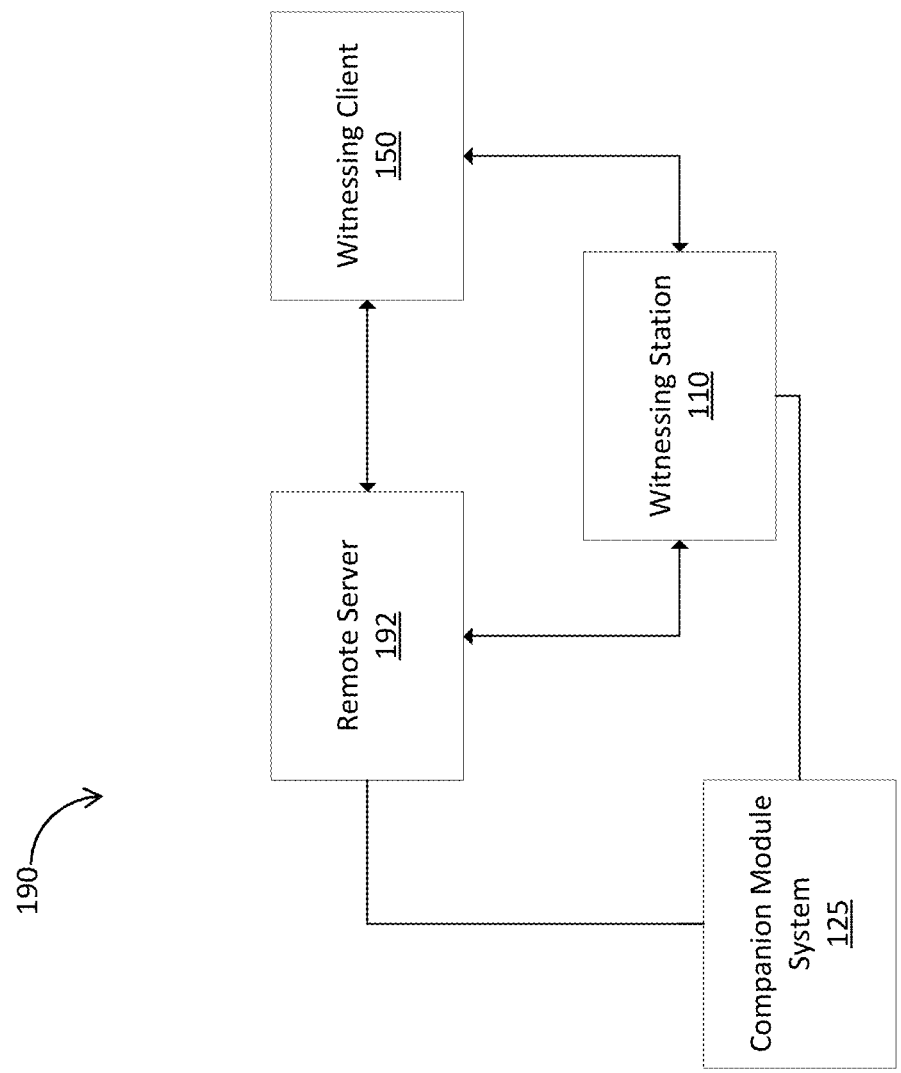

Referring to FIG. 1B, the witnessing device 110 may be part of a system 190 that includes a remote server 192, the witnessing device 110, a witnessing client 150 and the companion module system 125. The witnessing device 110 and the companion module system 125 may be an integrated unit or may be separate stations remote from one another. The witnessing device 110 and the witnessing client 150 may be part of separate units remote from one another. The witnessing device 110, the remote server 192, the witnessing client 150, and the companion module system 125 may be communicatively coupled to one another via a network. The network may be a wired and/or wireless network including, for example, a public land mobile network (PLMN), a local area network (LAN), a virtual local area network (VLAN), a wide area network (WAN), the Internet, a short range radio connection, for example Bluetooth, a peer-to-peer mesh network, and/or the like. The remote server 192, which may include a cloud-based server, may provide data and/or instructions from the witnessing device 110 to the companion module system 125 (e.g., the module controller 140 and/or one or more of the companion modules 145) to implement one or more features of the medical workflow consistent with implementations of the current subject matter. For example, the remote server 192 may coordinate access to or one or more functions performed by the at least one companion module 145. Additionally and/or alternatively, the remote server 192 may provide data and/or instructions from the witnessing device 110 to the witnessing client 150 and/or from the witnessing client 150 to the witnessing device 110. For example, the remote server 192 may coordinate the communication session between the witnessing device 110 and the witnessing client 150.

Figure 2:
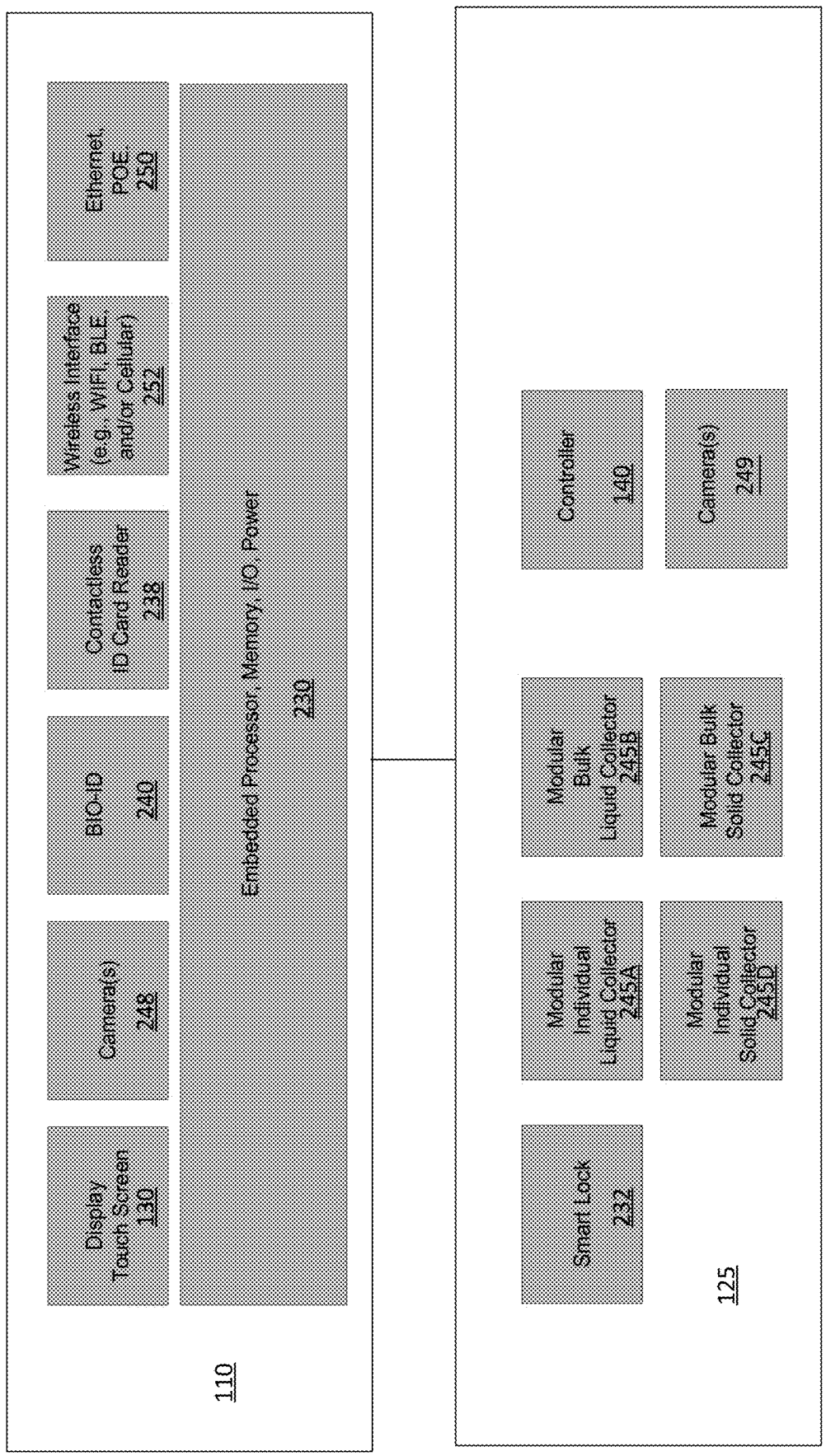
FIG. 2 is a block diagram depicting aspects of a witnessing system consistent with implementations of the current subject matter.

FIG. 2 is a block diagram depicting aspects of the witnessing device 110 and the companion module system 125 consistent with implementations of the current subject matter. The witnessing device 110 may include a controller 230 which controls the functions of the witnessing device 110. The controller 230 may include, for example one or more processors, one or more computers, one or more programmable logic controllers, and/or the like. The witnessing device 110 may also include the user interface 130, one or more cameras 248, a badge reader 238, an input/output device 250, and an antenna 252, which are described in more detail below.

The companion module system 125 may include at least one companion module 145 and the module controller 140. In some implementations, the module controller 140 may control one or more operations of the companion modules 145. Additionally and/or alternatively, each of the companion modules 145 may include the module controller 140. The companion modules 145 may include a modular individual liquid collector 245A, a modular bulk liquid collector 245B, a modular individual solid collector 245D, and a modular bulk solid collector 245C. Additionally, and/or alternatively, the companion modules 145 may include a smart lock 232, which may be coupled with or be positioned on one or more of the modular individual liquid collector 245A, the modular bulk liquid collector 245B, the modular individual solid collector 245D, and the modular bulk solid collector 245C. The module controller 140 may control one or more functions of the at least one companion module 145. For example, the module controller 140 may include actuators, for example, motors, solenoids, and/or the like. The module controller 140 may use the actuators to move mechanisms into a desired position. The module controller 140 may include sensors, for example, limit switches, optical sensors, tachometers, encoders, load cells, torque sensors, and/or the like. The module controller 140 may use the sensors to detect whether a mechanism is, for example, in position, out of position, moving, applying a force, applying a torque, and/or the like.

As noted above, the companion module system 125 may include separate collectors for collecting solid waste items and liquid waste items. The solid waste collectors may include the modular individual solid collector 245D and the modular bulk solid collector 245C. Similarly, the liquid collectors may include the modular individual liquid collector 245A and the modular bulk liquid collector 245B. a biometric scanner 240, In some implementations, the companion modules 245 may include moveable covers and/or shutters to provide access to and prevent access to one or more access points of each of the companion modules 245. The witnessing device 110 (such as via the controller 230) may communicate with the at least one companion module 245 (such as via the module controller 140) to control a position of the covers and/or shutters. The controller 230 may cause a cover and/or shutter of a companion module 245 to open during a witnessing session of the medical workflow to allow the waste to be placed in or poured into the corresponding companion module 245. After the waste is deposited, the controller 230 may cause the cover and/or shutter to close to prevent other items from being deposited and/or to prevent unauthorized removal of waste items from the particular companion module 245.

In some implementations, the at least one companion module 245 may each include a smart lock 232, which may secure and/or lock the at least one companion module 245. The smart lock 232 may be configured to release or engage based on multiple factors that are dynamically assessed. For example, the smart lock 232 may include location awareness to determine a current location of the smart lock 232. The smart lock 232 may consider one or more factors, such as the location along with the credentials of a user, type of medication involved in the medical workflow, the patient involved in the medical workflow, whether a secure connection has been established between the witnessing device 110 and the witnessing client 150, and the like, when the user requests access to the locked element. The smart lock 232 may determine, based on at least one of the factors, whether to release the smart lock 232. This ensures that only authorized personnel are allowed to access the locked element, that such access only takes place in an appropriate location, that such access only takes place during a secure witnessing session, and/or that the witness may properly observe the medical workflow during the witnessing session. The appropriate location may include, for example, a testing room or other facility with monitoring that can be used to ensure the security of the companion modules 145, and that the companion modules 145 and waste items stored therein are not tampered with and/or diverted. The smart lock 232 may include additional and/or other sensors. For example, the smart lock 232 may include a temperature sensor to record the environment around the locked element. This temperature information may affect the results of tests performed on waste items stored in the locked element. The smart lock 232 may include a memory element to store the sensor, location, time, and/or other information detected or generated by the smart lock 232. The smart lock 232 may include a communications module for transmitting sensor data along with access requests.

The witnessing device 110 may determine, based on one or more of: the wasting user, witnessing user, wasting location, substance being wasted, or other property detectable or accessible by the witnessing device 110, which companion module 145 to operate during the medical workflow. For example, if the substance being wasted is an uncontrolled solid (e.g., excess ibuprofen), the risk of diversion may be less than when wasting a controlled substance such as oxycodone. As another example, if the substance being wasted is an uncontrolled liquid (e.g., excess acetaminophen), the risk of diversion may be less than when wasting a controlled substance such as fentanyl. In some implementations, a risk score may be generated based on one or more of: the wasting user, witnessing user, wasting location, substance being wasted, or other property detectable or accessible by the witnessing device 110. If the risk score corresponds to a threshold, the substance being wasted may be directed to a particular companion module 145 by unlocking the particular companion module 145 or otherwise indicating to the clinician (such as via the user interface 130) that the substance being wasted should be directed to the particular companion module 145. In some implementations, if the risk score, behavior of the wasting user and/or the witnessing user, the wasting location, the substance being wasted, and/or another property detectable or accessible by the witnessing device 110, corresponds to a threshold, such as over a predetermined period of time (e.g., one day, one week, one month, one year, and the like), and/or after a predetermined number of witnessed wasting events (e.g., one, two, three, four, five, ten, twenty, thirty, forty, fifty, one-hundred, or more and/or other ranges therebetween), the witnessing device 110 may determine that a witness, such as the witnessing user, is no longer necessary to witness one or more parts of the medical workflow, such as the retrieval, administration, and/or disposal of medication. In other words, based on the risk score, behavior of the wasting user and/or the witnessing user, the wasting location, the substance being wasted, and/or another property detectable or accessible by the witnessing device 110, the witnessing device 110 may determine that the witnessing user may be removed from at least a part of the medical workflow. Thus, in some situations, the witness may not be necessary during at least a part of the medical workflow, and as a result, based on the risk score, behavior of the wasting user and/or the witnessing user, the wasting location, the substance being wasted, and/or another property detectable or accessible by the witnessing device 110, the witnessing session may not be initiated at the witnessing client and/or at least the part of the medical workflow may not be recorded. Features for generating risk scores are described in, for example, U.S. Patent Publication No. US20170109497A1 entitled "Controlled substance diversion detection systems and methods," commonly owned and assigned, which is incorporated by reference in its entirety.

With continued reference to FIG. 2, the witnessing device 110 may be a standalone unit (e.g., a kiosk or a mobile cart). Alternatively, the witnessing device 110 may be wall mounted. Additionally and/or alternatively, the witnessing device 110 may be mounted above a sink or other disposal location. Additionally and/or alternatively, the witnessing device 110 may be mounted to and/or attached to another device, such as one or more of the companion modules 145.

The witnessing device 110 may include one or more recording devices, shown as camera 248. Similarly, the companion module system 125 may include one or more modular recording devices, shown as camera 249. The cameras 248, 249 may be used to monitor and/or record the medical workflow, including recording video, images, and/or audio of the person who performs the medical workflow, the medical workflow itself, and/or the witness observing the medical workflow via the witnessing client 150. In some implementations, the camera 248 of the witnessing device 110 may record at least the face of the user of the witnessing device 110 during the medical workflow, such as when the user accesses the witnessing device 110, while the camera 249 may record one or more other aspects of the medical workflow, such as the user placing a waste item in one or more of the companion modules 145 of the companion module system 125. As another example, the camera 249 may be used to record video of the waste item as it is placed in a collection receiver or access point, for example, at the modular individual liquid collector 245A, the modular bulk liquid collector 245B, the modular bulk solid collector 245C, and/or the modular individual solid collector 245D. The one or more cameras 248, 249 may be used for image analysis of a solid and/or liquid waste item. Image analysis of the waste item may include identification of medications based on, for example, color, size, shape, and/or markings.

The witnessing device 110 may include one or more auditing features, which may allow the witnessed medical workflow to be more easily tracked. For example, the witnessing device may allow for the medical workflow (e.g., waste, withdrawal, and the like) to be tracked and associated with a user, for example, the clinician 135 and/or the witness 155. For example, the witnessing device 110 may record information collected when waste is deposited, including the identification tag (barcode, RFID tag, etc.), the identity of the clinician 135 who deposited the waste, the identity of the witness 155 who witnessed the clinician depositing the waste, videos recorded during the wasting process, and physical property measurements taken during the wasting process. For example, the witnessing device 110 may include a badge reader 238 for reading an identification code of the clinician 135 and/or a biometric scanner 240 for obtaining biometric features of the clinician 135 when the clinician 135 accesses the witnessing device 110, initiates the medical workflow, and/or during a witnessing session. The witnessing device 110 and/or one of the companion modules 145 may include a label scanner to scan the label of the medication, waste, and/or the companion module in which the waste was deposited or retrieved from. The scanned label may be used as part of the record created of the medical workflow and may be linked to or associated with the clinician 135 and/or the witness 155 for tracking and auditing purposes. The record of the medical workflow may also include time and date details to associate timing with the wasting process.

In some implementations, the witnessing device 110 includes an input/output device 250, which may provide input/output operations for a network device. For example, the input/output device 250 may include Ethernet ports or other networking ports to communicate with one or more wired and/or wireless networks (e.g., a local area network (LAN), a wide area network (WAN), the Internet), and/or to communicate with one or more of the companion modules 145. The witnessing device 110 may additionally and/or alternatively include an antenna 252 for communicating view a network including, for example, a public land mobile network (PLMN), a local area network (LAN), a virtual local area network (VLAN), a wide area network (WAN), the Internet, a short range radio connection, for example a BLUETOOTH® compatible connection, a peer-to-peer mesh network, or the like.

Consistent with implementations of the current subject matter, if the clinician 135 is suspected of diverting medications and/or the witnessing session is not properly established or disconnects during the medical workflow, the witnessing device 110 may flag the medical workflow.

Figure 3:
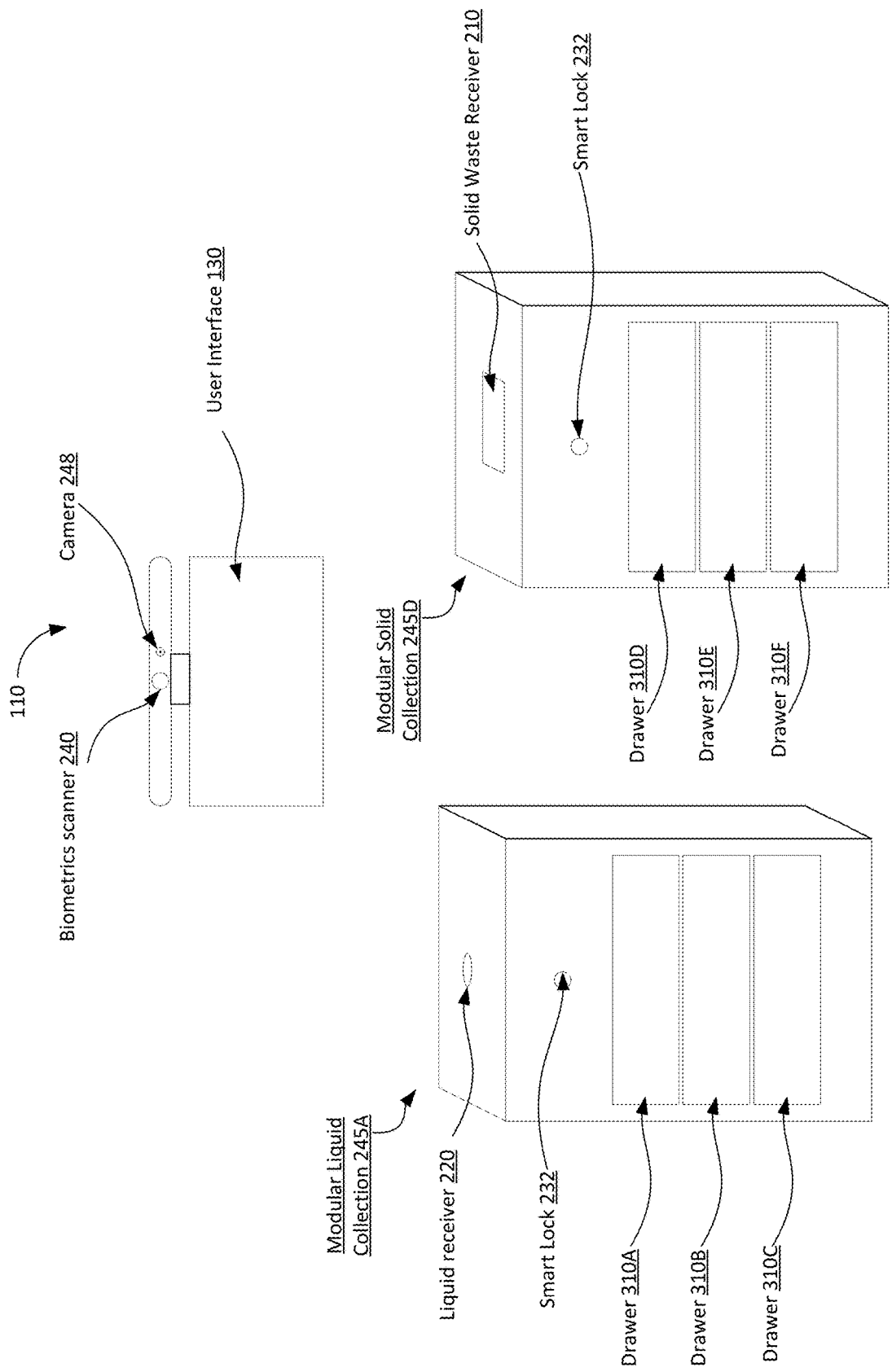
FIG. 3 is a diagram depicting an exemplary witnessing device and module system consistent with implementations of the current subject matter.

FIG. 3 is a diagram depicting an exemplary witnessing device 110 and one or more exemplary companion modules 145, such as the modular individual liquid collector 245A, and the modular individual solid collector 245D, consistent with implementations of the current subject matter. The size, shape, and form of the witnessing device 110 and/or the companion modules 145 shown in FIG. 3 is exemplary and non-limiting; the witnessing device 110 and/or the companion modules 145 consistent with implementations of the current subject matter may be of various different sizes, shapes, and forms.

Shown in FIG. 3 is the user interface 130, which may be integrated as part of the witnessing device 110. The user interface 130 may guide the clinician 135 through the medical workflow, including, for example, authenticating the user, securing the waste item, dispensing medication, administering medication, obtaining consent from a patient, connecting with a remote witness via the witness client, causing one or more of the companion modules 145 to perform operations (e.g., locking, unlocking, issuing an alert), and/or depositing waste into an access point of one or more of the companion modules 145 of the witnessing device 110. Also shown in the representation of the witnessing device 110 of FIG. 3 are the biometrics scanner 240 and the camera 248.

As noted above, the witnessing device 110 may be communicatively coupled with the companion modules 145 of the companion module system 125. FIG. 3 illustrates an example of the modular individual liquid collector 245A and the modular individual solid collector 245D. As shown, the modular individual liquid collector 245A may include the smart lock 232. The modular individual liquid collector 245A may include a liquid receiver 220 through which the liquid waste may be deposited. The modular individual liquid collector 245A may include one or more drawers, such as drawer 310A, drawer 310B, and drawer 310C. The drawers 310A, 310B, and 310C may include one or more collection bins and/or passages to other bins. The smart lock 232 on the modular individual liquid collector 245A, for example, may control access to the drawers 310A, 310B, and 310C.

In some implementations, the modular individual solid collector 245D may also include the smart lock 232. The modular individual solid collector 245D may include a solid receiver 210 through which the solid waste may be deposited. The modular individual solid collector 245D may include one or more drawers, such as drawer 310D, drawer 310E, and drawer 310F. The drawers 310D, 310E, and 310F may include one or more collection bins and/or passages to other bins. The smart lock 232 on the modular individual solid collector 245D, for example, may control access to the drawers 310D, 310E, and 310F.

Figure 4:
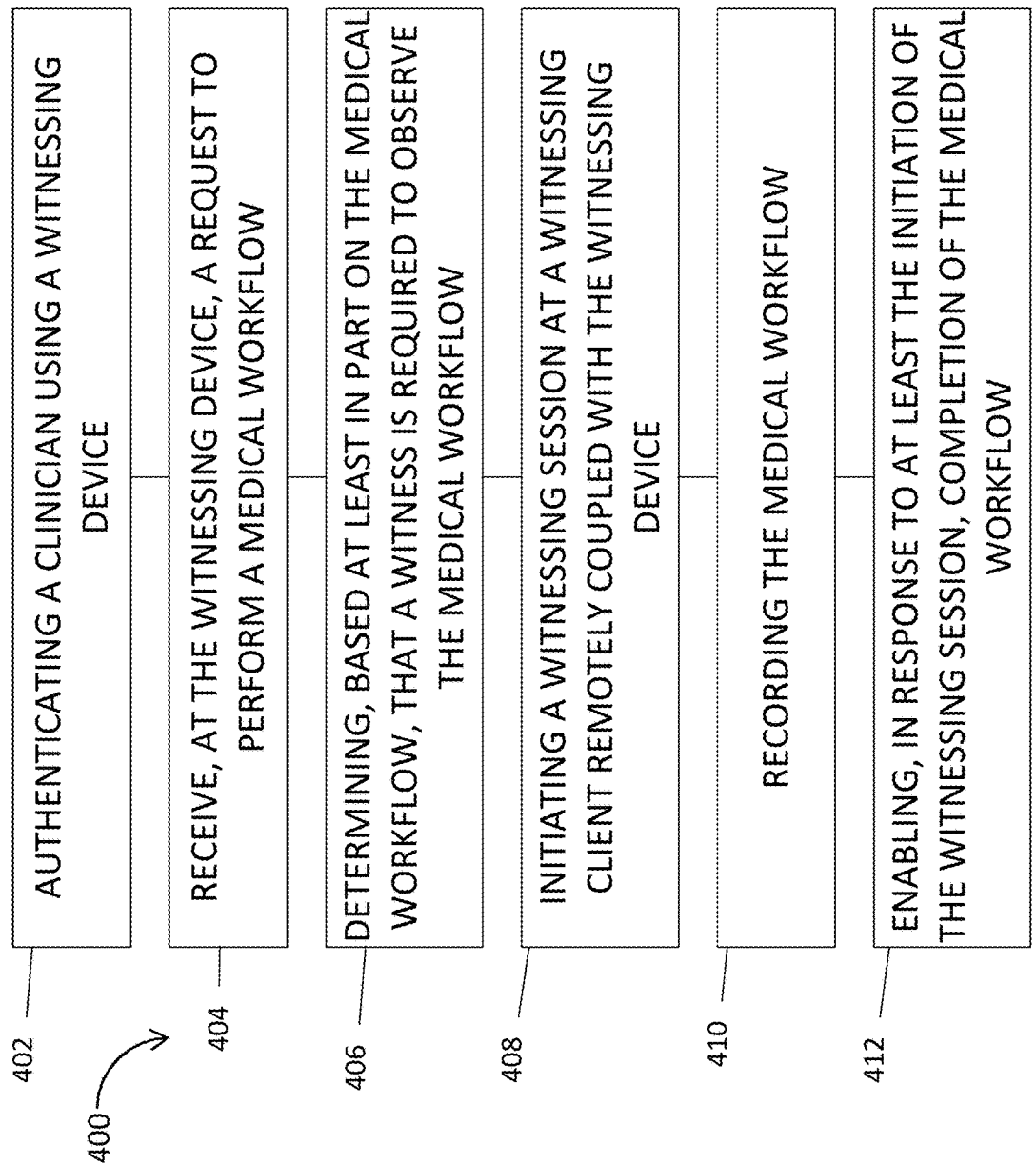
FIG. 4 is a flowchart illustrating a process consistent with implementations of the current subject matter.

FIG. 4 depicts a flowchart illustrating a process 400 consistent with implementations of the current subject matter. Referring to FIG. 4, at 402, the witnessing device 110 may authenticate the clinician 135 using the witnessing device 110. The clinician 135 may be prompted to, for example, enter a user name and password, provide a fingerprint scan, provide a retina scan, swipe an employee card, or provide other information, for example, biometric information, to verify the clinician 135 is authorized to use the witnessing device 110.

At 404, the witnessing device 110 may receive a request to perform a medical workflow. The medical work flow may include wasting a medication, dispensing a medication, administering a medication, and/or obtaining consent from a patient. The request may be received by the witnessing device 110, for example, via the user interface 130. In some implementations, the request may be a selection of at least one option presented to the clinician 135 via the user interface 130 of the witnessing device 110. The request may include a selection of a type of workflow from the at least one option presented to the clinician. Additionally and/or alternatively, the request may be received via another input coupled with the witnessing device 110, such as via the companion module system 125.

At 406, based at least in part on the request to perform the medical workflow, the witnessing device 110 (e.g., the controller 230) may determine that a witness (e.g., the witness 155) is required to observe the medical workflow. For example, in some circumstances, the witness may be required to observe the performance of the medical workflow, the medication involved in the medical workflow, the patient involved in the medical workflow, the clinician involved in the medical workflow, and/or the like.

A witness (in addition to the clinician) may be required to view certain medical workflows, such as wasting medications, dispensing medications, administering medications, and/or obtaining consent from a patient. For example, the witnessing device 110 may determine that the type of medical workflow requested is a type that requires a witness. The types of medical workflows that require a witness may include wasting medications, dispensing medications, administering medications, and/or obtaining consent from a patient. Additionally and/or alternatively, the witnessing device 110 may determine that a witness is required to observe the medical workflow based at least in part on the type of medication involved. For example, based on the received request via the user interface, a scan of the medication, and/or another input, the witnessing device 110 may determine that the medication involved in the medical workflow is a controlled and/or hazardous medication, a particular type of vaccine, or other flagged type of medication. Based on the determination that the medication is a controlled and/or hazardous medication, the particular type of vaccine, or other flagged type of medication, the witnessing device 110 may determine that a witness is required to observe the medical workflow.

Additionally and/or alternatively, the witnessing device 110 may determine that a witness is required to observe the medical workflow based at least in part on the identity of the clinician accessing the witnessing device 110. For example, based on the received request via the user interface, a scan of the clinician's badge, biometric data, and/or the like, the witnessing device may access data associated with the clinician. The data associated with the clinician may include the clinician's name, credentials, training history, education, treatment history, past behavior, level of experience, job title, and/or the like. As noted above, the witnessing device 110 may determine whether the clinician should be witnessed based on a risk score associated with the clinician. The risk score may be generated based on the data associated with the clinician, such as employment type, length of employment, history of wasting processes in which the clinician has been involved, and/or age of the clinician. Based on the data associated with the clinician and/or the risk score (e.g., the risk score reaching and/or exceeding a threshold), the witnessing device 110 may determine that the clinician involved in the medical workflow requires a witness to observe the clinician performing the medical workflow. Alternatively or additionally, the witnessing device 110 may determine that a witness is required to observe the medical workflow based on a duration since a previous witnessing session for the clinician, for example, if the duration exceeds a threshold duration.

Additionally and/or alternatively, the witnessing device 110 may determine that a witness is required to observe the medical workflow based at least in part on the particular patient involved. For example, based on the received request via the user interface, entry of a patient identifier and/or the like, the witnessing device may access data associated with the patient being treated or being cared for within the vicinity of the witnessing device 110. The data associated with the patient may include the patient's name, medication associated with the patient, the patient's treatment history, the patient's age, the patient's medical history, and/or the like. Based on the data associated with the patient, the witnessing device 110 may determine that the medical workflow requires a witness to observe the clinician performing the medical workflow.

Alternatively or additionally, the witnessing device 110 may determine that a witness is required to observe the medical workflow based at least in part on an availability of resources and/or resource capacity at the witnessing device 110 and/or the companion module system 125 to perform the witnessing. The resource availability and/or resource capacity may include, for example, video and/or image memory availability, availability of receiving containers and/or waste containers (e.g., companion modules 145), connectivity to the remote witnessing client, availability of live witnesses located at the medical facility, and/or the like. For example, if no witnesses are available at the medical facility, the witnessing device 110 may utilize remote witnessing capabilities. Additionally, and/or alternatively, the witnessing device 110 may determine that a witness is required to observe the medical workflow based on a generated pseudorandom number.

At 408, the witnessing device 110 may initiate a witnessing session at the witnessing client 150. For example, the witnessing device 110 may initiate a witnessing session at the witnessing client 150 in response to determining that a witness is required to observe the medical workflow. In some implementations, the witnessing device 110 may initiate a witnessing session at the witnessing client 150 in response to receipt of a request to initiate the witnessing session via the user interface of the witnessing device. As noted above, the witnessing device 110 may initiate the witnessing session at the witnessing client 150, based at least in part on the identity of the clinician, the identity of the patient, the type of medication, a pseudorandom number, a duration since a previous witnessing session for the clinician, resource capacity, and/or the like.

In some implementations, initiating the witnessing session may include providing access to the witness to observe the medical transaction from the witnessing client via the witnessing device. As noted above, the witnessing client may be coupled with a remote server or a web-based application programming interface that is remote (e.g., physically remote) from the witnessing device. In some implementations, during the initiation of the witnessing session at the witnessing client, the witnessing device may establish a connection with the witnessing client. The witnessing client may display the request to establish the connection with the witnessing device, and the witnessing client may receive the acceptance of the request to establish the connection.

In some implementations, initiating the witnessing session may also include establishing a connection with at least one companion module 145 of the companion module system (e.g., the companion module system 125). For example, the witnessing device may establish a connection with one or more particular companion modules 145, based on the medical workflow. For example, if the medical workflow includes wasting a medication or other substance, the witnessing device may establish a connection with the individual liquid collector, the modular bulk liquid collector, the modular individual solid collector, the modular bulk solid collector, and/or the like. As another example, the witnessing device may establish a connection with one or more cameras positioned on one of the companion modules 145 and/or positioned at various locations within the patient care room to observe and/or record the medical workflow.

In some implementations, the witnessing device 110 may include features to maintain integrity of the witnessing processes before initiating a session or when one or more features fail. The witnessing device 110 may include a configuration file identifying operational state of elements needed for a witnessing session. If the elements are not in the operational state, the witnessing device 110 may disable one or more aspects of the medical workflow, such as the wasting process. Some elements may be controlled by the witnessing device 110. In such instances, if the element is not in the specified state, the witnessing device 110 may transmit a control signal to adjust the element to the required state. For example, if the configuration specifies that the witnessing device 110 be connected to a specific network or have visibility to a specific network address, the witnessing device 110 may transmit a message to activate a transceiver to connect to the specific address. Examples of other elements that may be required for specific configurations include at least one companion module 145, such as a camera, a display, one or more sensors, a supply of wasting containers, or other element associated with the witnessing device 110. A similar operational readiness verification may be performed by a witnessing client before establishing a connection therewith and then periodically during the witnessing session. If an event is detected that causes the operational state to violate the configuration (e.g., loss of network connectivity), the device may secure at least one companion module 145, such as a wasting station, until the appropriate state is achieved. For example, if the access point at the at least one companion module 145 is unsecured and, while unsecured but before receiving the wasting container, network connectivity with the remote witnessing client is lost, the witnessing device 110 may transmit a message to secure the access point until the connection is reestablished. The connection may be reestablished using a preconfigured connection protocol such as, or similar to, HTTP, FTP, session initiation protocol (SIP), real-time transport protocol (RTP), secure real-time transport protocol (SRTP), ITU-T H.323, or media gateway control protocol (MGCP). The state of the witnessing session may be stored by the witnessing device 110 and used to continue an interrupted witnessing session. For example, an identifier for the witnessing session may be stored in a data store accessible to the device(s). One or more identifiers for the device(s), user(s), and witnessing step(s) performed or outstanding may be stored in association with the identifier. Reconstruction may include attempting to establish the connection between the devices associated with the session identifier (if the session was a remote witnessing session), confirming the user identities, and configuring the device(s) to perform the next required step.

At 410, the witnessing device 110 may record and/or store the medical workflow and data associated with the medical workflow. For example, via one or more cameras coupled with the witnessing device positioned on one or more of the companion modules and/or at various locations in the patient care room, the witnessing device may record videos, images, and/or audio of the medical workflow, the face of the clinician, and/or the face of the witness, and data associated with the medical workflow, including a time stamp.

Additionally and/or alternatively, before, during, and/or after recording the medical workflow, the witnessing device may determine that the medical workflow is accessible to the witness via the witnessing client. For example, the witnessing device may communicate with the cameras and/or companion modules to determine whether the medical workflow is visible. In this example, the cameras, sensors, and/or other devices coupled with the witnessing device may scan the patient care room, a particular location within the patient care room, and/or the like to detect whether that the clinician, the patient, the medication, and/or the corresponding companion module is within the field of view of the cameras. Based on the scan, the witnessing device may determine whether the cameras are at least partially occluded. Additionally and/or alternatively, the witnessing device may detect whether the medical workflow is visible to the clinician and/or the witness, or determine that the cameras are at least partially occluded, based on an input received at the user interface of the witnessing device, an input received at the user interface of the witnessing client, and/or the like. For example, the user interface of the witnessing device and/or the witnessing client may display a prompt, video, and/or images as part of a request for an input by the clinician and/or witness as to whether the desired location is visible.

If the witnessing device determines that the cameras are at least partially occluded, the witnessing device may disable the medical workflow and/or otherwise prevent the medical workflow from proceeding until the medical workflow is fully visible (e.g., to the witness via the witnessing client). In some implementations, if the witnessing device determines that the cameras are at least partially occluded, the witnessing device (e.g., the controller 230) may trigger an alert, which may include a notification that may be provided via a user interface of the witnessing device. For example, the notification may be provided via a short messaging service (SMS) text, an email, a webpage, an application, and/or the like. Additionally and/or alternatively, in response to the detection of an occluded field of view, the witnessing device may cause an increase in a sampling rate of one or more of the cameras, record video and/or images in color, rather than in black and white, divert additional electronic and/or memory resources to the cameras, and/or the like.

At 412, in response to at least the initiation of the witnessing session, the witnessing device may enable the medical workflow to be completed. For example, the witnessing device may trigger a completion event at one or more of the companion modules. The completion event may depend on the medical workflow. As an example, if the medical workflow includes wasting a medication, the completion event may include unlocking the corresponding companion module (e.g., the individual liquid collector, the modular bulk liquid collector, the modular individual solid collector, the modular bulk solid collector, and/or the like) to allow the medication to be deposited. In this example, the witnessing device (e.g., via the controller) may communicate with the corresponding companion module to open a cover, allowing the clinician to access an access point to deposit the waste. The witnessing device may then prompt the clinician to deposit or pour the waste into the opened companion module.

As another example, if the medical workflow includes administering a medication, the completion event may include unlocking a drawer of the corresponding companion module (e.g., the dispensing cabinet) to allow the medication to be withdrawn. In this example, the witnessing device (e.g., via the controller) may communicate with the corresponding companion module to open the drawer, allowing the clinician to access an access point to withdraw the medication. The witnessing device may then prompt the clinician to withdraw the medication (e.g., a certain type and/or dose). Additionally and/or alternatively, the completion event may include prompting the clinician, via the user interface of the witnessing device, to administer the medication to the medication to the patient.

The witnessing device (e.g., via the controller) may determine that the medical workflow has been completed. In some implementations, upon determining that the medical workflow has been completed, the witnessing device (e.g., via the controller) may lock the drawer, bin, and/or the like, thus preventing further access to the access points. Consistent with implementations of the current subject matter, the controller may preventing further access to the access points after a predetermined period of time has elapsed. The predetermined period of time may be chosen such that there is sufficient time to for example, deposit the waste, withdraw the medication, and the like. The predetermined period of time may be based on the item being deposited, withdrawn, and/or administered. For example, if the waste is a bag that is being deposited, less time may be allotted than that for a vial of medication being directly emptied. The predetermined periods of time may be based on data indicating time allotments for various waste items.

In some implementations, upon determining that the medical workflow has been completed, the witnessing device 110 may receive a witnessing record. The witnessing record may be received, at least in part, from the witnessing client 150. The witnessing record may include the identity of the witness 155 who witnessed the wasting process. The witnessing record may include information indicating that the witnessing was remote. The witnessing record may include time data identifying when the witnessing was requested and how soon the witness confirmed completion of the medical workflow. In some implementations, the witnessing record may be generated, at least in part, by the witnessing device 110.

In some implementations, upon determining that the medical workflow has been completed, the witnessing device 110 may receive the recording and/or data associated with the medical workflow. The recording and/or associated data may be received, at least in part, from the at least one companion module. For example, information related to the clinician, the medication, the patient, the companion module, and/or the medical workflow (e.g., type of waste, type of medical workflow, type of companion module, time date, etc.) may be part of the recording. Consistent with implementations of the current subject matter, the data may include, for example, an identifier associated with the waste, the identity of the clinician who performed the medical workflow, the witnessing record received from the witnessing client 150, video and/or still images of the medical workflow, and/or the like.

Consistent with implementations of the current subject matter, the type of the medication wasted, deposited, withdrawn, and/or administered may be associated with the clinician. For example, the witnessing device may communicate with the corresponding companion module (e.g., dispensing cabinet) and may track the medication initially dispensed to the clinician. When the clinician is authenticated at the witnessing device, the witnessing device may know the medication that has been dispensed to the clinician. Consistent with implementations of the current subject matter, the witnessing device may determine the medication type by receiving a medication identifier, from, for example, a scanning device such as a barcode reader or scanner, associated with the medication.

In some implementations, upon determining that the medical workflow has been completed, the witnessing device may generate an alert indicating that the medical workflow has been completed. An alert may include a notification that may be provided via a user interface at the witnessing device, the witnessing client, and/or the at least one companion module. For example, the notification may be provided via a short messaging service (SMS) text, an email, a webpage, an application, and/or the like.

Accordingly, the witnessing system may help to reduce or eliminate the possibility that a witness will be unavailable during a medical workflow, reduce or eliminate predatory medical practices, and/or reduce or eliminate diversion of medication. The witnessing system may also produce verifiable records of various aspects of the witnessed medical workflow, which provides an audit trail of the witnessing, including, for example, recorded video, images, audio, and/or other data associated with the medical workflow. The witnessing device may also communicate with at least one companion module within the patient care area, which may help clinicians properly dispose of medication, capture various views of the medical workflow, and/or the like. The witnessing device may also provide instructions to the clinician and/or witness to help ensure that the medical workflow is performed properly.

FIG. 5 depicts a block diagram illustrating a computing system 500 consistent with implementations of the current subject matter. Referring to FIG. 1A, FIG. 1B, and FIG. 2, the computing system 500 may be used to implement one or more components of the witnessing system 100, for example, the various components of the witnessing device 110.

As shown in FIG. 5, the computing system 500 may include a processor 510, a memory 520, a storage device 530, and input/output device 540. The processor 510, the memory 520, the storage device 530, and the input/output device 540 may be interconnected via a system bus 550. The processor 510 is capable of processing instructions for execution within the computing system 500. Such executed instructions may implement one or more components of the witnessing system 100, for example, the witnessing device 110. In some example embodiments, the processor 510 may be a single-threaded processor. Alternatively, the processor 510 may be a multi-threaded processor. The processor 510 is capable of processing instructions stored in the memory 520 and/or on the storage device 530 to display graphical information for a user interface provided via the input/output device 540.

The memory 520 is a computer readable medium such as volatile or non-volatile that stores information within the computing system 500. The memory 520 may store data structures representing configuration object databases, for example. The storage device 530 is capable of providing persistent storage for the computing system 500. The storage device 530 may be a floppy disk device, a hard disk device, an optical disk device, a tape device, a solid-state device, and/or any other suitable persistent storage means. The input/output device 540 provides input/output operations for the computing system 500. In some implementations, the input/output device 540 includes a keyboard and/or pointing device. In various implementations, the input/output device 540 includes a display unit for displaying graphical user interfaces.

According to some implementations, the input/output device 540 may provide input/output operations for a network device. For example, the input/output device 540 may include Ethernet ports or other networking ports to communicate with one or more wired and/or wireless networks (e.g., a local area network (LAN), a wide area network (WAN), the Internet).

In some implementations, the computing system 500 may be used to execute various interactive computer software applications that may be used for organization, analysis, and/or storage of data in various formats. Alternatively, the computing system 500 may be used to execute any type of software applications. These applications may be used to perform various functionalities, e.g., planning functionalities (e.g., generating, managing, editing of spreadsheet documents, word processing documents, and/or any other objects, etc.), computing functionalities, communications functionalities, etc. The applications may include various add-in functionalities or may be standalone computing products and/or functionalities. Upon activation within the applications, the functionalities may be used to generate the user interface provided via the input/output device 540. The user interface may be generated and presented to a user by the computing system 500 (e.g., on a computer screen monitor, etc.).

One or more aspects or features of the subject matter described herein may be realized in digital electronic circuitry, integrated circuitry, specially designed ASICs, field programmable gate arrays (FPGAs) computer hardware, firmware, software, and/or combinations thereof. These various aspects or features may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which may also be referred to as programs, software, software applications, applications, components, or code, include machine instructions for a programmable processor, and may be implemented in a high-level procedural and/or object-oriented programming language, and/or in assembly/machine language. As used herein, the term "machine-readable medium" refers to any computer program product, apparatus and/or device, for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium may store such machine instructions non-transitorily, for example as would a non-transient solid-state memory or a magnetic hard drive or any equivalent storage medium. The machine-readable medium may alternatively or additionally store such machine instructions in a transient manner, for example, as would a processor cache or other random access memory associated with one or more physical processor cores.

To provide for interaction with a user, one or more aspects or features of the subject matter described herein may be implemented on a computer having a display device, for example a cathode ray tube (CRT) or a liquid crystal display (LCD) or a light emitting diode (LED) monitor for displaying information to the user and a keyboard and a pointing device, for example a mouse or a trackball, by which the user may provide input to the computer. Other kinds of devices may be used to provide for interaction with a user as well. For example, feedback provided to the user may be any form of sensory feedback, for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

Although the disclosure, including the figures, described herein may describe and/or exemplify different variations separately, it should be understood that all or some, or components of them, may be combined.

Although various illustrative embodiments are described above, any of a number of changes may be made to various embodiments. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as, for example, "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise" and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, are possible.

In the descriptions above and in the claims, phrases such as, for example, "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, web services, or rich site summary (RSS). In some embodiments, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for witnessing wasting a medication, the system comprising:
    at least one data processor, and at least one memory storing instructions which, when executed by the at least one data processor, result in operations comprising:
    authenticating, at a witnessing device, a clinician, wherein the witnessing device comprises or is comprised in the at least one data processor and the at least one memory;
    receiving, at the witnessing device, a request to perform a medical workflow, wherein the medical workflow comprises a series of one or more steps for wasting the medication;
    determining, at the witnessing device and based at least in part on the medical workflow, that a witness is required to observe the medical workflow;
    in response to the determining that the witness is required, initiating, by the witnessing device at a witnessing client, a witnessing session at the witnessing client configured to allow the witness to remotely observe the medical workflow; and
    in response to at least the initiation of the witnessing session, enabling, by the witnessing device, completion of the medical workflow by providing a command to at least one companion device to enable wasting of the medication by unlocking the at least one companion device;
    determining an elapsed time from the unlocking of the at least one companion device and/or wasting of the medication is completed; and
    relocking the at least one companion device to prevent access to the at least one companion device responsive to the elapsed time.

2. The system of claim 1, wherein the at least one companion device includes one or more of a smart lock, a waste container, a dispensing cabinet, and a camera.

3. The system of claim 1, wherein authenticating the clinician comprises verifying an identity of the clinician as an authorized user.

4. The system of claim 1, wherein the determination that the witness is required to observe the medical workflow is based at least on a type of medication involved in the medical workflow.

5. The system of claim 1, wherein the determination that the witness is required to observe the medical workflow is based at least on the clinician performing the medical workflow.

6. The system of claim 1, further comprising:
the witnessing client; and
a remote server by which the witnessing device communicates with the witnessing client.

7. The system of claim 6, further comprising:
at least one companion device communicatively coupled with the witnessing device for use during the medical workflow.

8. The system of claim 1, wherein the witnessing device comprises a user interface, wherein the user interface provides information and/or instructions related to the authentication, the medical workflow, and/or the witnessing session.

9. The system of claim 1, wherein operations further comprise:
generating, at the witnessing client, a witnessing record in response to completion of the witnessing session, wherein the witnessing record further comprises at least one of an identity of the witness, information indicating that the witnessing was remote, time data identifying when the witnessing session was requested, or time data identifying how soon a witness confirmed completion of the medical workflow.

10. The system of claim 1, wherein the determination that the witness is required to observe the medical workflow comprises:
generating a risk score based on at least one of a wasting user, a witnessing user, a wasting location, or a substance being wasted; and
determining whether the generated risk score exceeds a pre-determined threshold.

11. The system of claim 1, wherein the medical workflow further comprises one or more steps for dispensing a medication, administering a medication, or obtaining consent from a patient; and wherein the command to the at least one companion device triggers a completion event for one or more steps of the medical workflow.

12. A method for witnessing wasting a medication, the method comprising:
authenticating, at a witnessing device, a clinician;
receiving, at the witnessing device, a request to perform a medical workflow, wherein
the medical workflow comprises a series of one or more steps for wasting the medication;
determining, at the witnessing device and based at least in part on the medical workflow, that a witness is required to observe the medical workflow;
in response to the determining that the witness is required, initiating, by the witnessing
device at a witnessing client, a witnessing session at the witnessing client configured to allow the witness to remotely observe the medical workflow;
in response to at least the initiation of the witnessing session, enabling, by the witnessing device, completion of the medical workflow by providing a command to at least one companion device to enable wasting of the medication by unlocking the at least one companion device;
determining an elapsed time from the unlocking of the at least one companion device and/or wasting of the medication is completed; and
relocking the at least one companion device to prevent access to the at least one companion device.

13. The method of claim 12, wherein the at least one companion device includes one or more of a smart lock, a waste container, a dispensing cabinet, and a camera.

14. The method of claim 12, wherein the determination that the witness is required to observe the medical workflow is based at least on one or more of a type of medication involved in the medical workflow and the clinician performing the medical workflow.

15. The method of claim 12, further comprising:
generating, at the witnessing client, a witnessing record in response to completion of the witnessing session, wherein the witnessing record further comprises at least one of an identity of the witness, information indicating that the witnessing was remote, time data identifying when the witnessing session was requested, or time data identifying how soon a witness confirmed completion of the medical workflow.

16. The method of claim 12, wherein the determination that the witness is required to observe the medical workflow comprises:
generating a risk score based on at least one of a wasting user, a witnessing user, a wasting location, or a substance being wasted; and
determining whether the generated risk score exceeds a pre-determined threshold.

17. A non-transitory computer-readable storage medium including program code, which when executed by at least one data processor, cause operations comprising:
authenticating, at a witnessing device, a clinician;
receiving, at the witnessing device, a request to perform a medical workflow, wherein the medical workflow comprises a series of one or more steps for wasting a medication;
determining, at the witnessing device and based at least in part on the medical workflow, that a witness is required to observe the medical workflow;
in response to the determining that the witness is required, initiating, by the witness device at a witnessing client, a witnessing session at the witnessing client configured to allow the witness to remotely observe the medical workflow;
in response to at least the initiation of the witnessing session, enabling, by the witnessing device, completion of the medical workflow by providing a command to at least one companion device to enable wasting of the medication by unlocking the at least one companion device;
determining an elapsed time from the unlocking of the at least one companion device and/or wasting of the medication is completed;
relocking the at least one companion device to prevent access to the at least one companion device; and
generating, at the witnessing client, a witnessing record in response to completion of the witnessing session, wherein the witnessing record comprises at least one of an identity of the witness, information indicating that the witnessing was remote, time data identifying when the witnessing session was requested, or time data identifying how soon a witness confirmed completion of the medical workflow.

* * * * *